United States Patent [19]

Osman

[11] 4,167,489
[45] Sep. 11, 1979

[54] LIQUID CRYSTALLINE COMPOUNDS

[75] Inventor: Maged A. Osman, Zurich, Switzerland

[73] Assignee: BBC Brown Boveri & Company, Limited, Baden, Switzerland

[21] Appl. No.: 882,742

[22] Filed: Mar. 2, 1978

[30] Foreign Application Priority Data

Mar. 8, 1977 [CH] Switzerland .................. 2861/77

[51] Int. Cl.$^2$ .................. C02F 1/13; C09K 3/34; C07C 121/60; C07C 121/64
[52] U.S. Cl. .................. 252/299; 252/408; 260/463; 260/465 B; 260/465 D; 260/465 E; 260/465 F; 350/350; 560/19; 560/24; 560/30; 560/61; 560/62; 560/64; 560/65; 560/73; 560/74; 560/83; 560/85; 560/86; 560/88; 560/108
[58] Field of Search .............. 560/73, 108; 252/299, 252/408; 250/350; 260/465 D, 465 E, 465 F, 465 B, 463

[56] References Cited

U.S. PATENT DOCUMENTS

| | | | |
|---|---|---|---|
| 3,827,780 | 8/1974 | Labes | 252/408 |
| 3,951,846 | 4/1976 | Gavrilovic | 252/299 |
| 3,960,752 | 6/1976 | Klanderman et al. | 252/299 |
| 3,983,049 | 9/1976 | Aftergut et al. | 252/299 |
| 4,001,137 | 1/1977 | Steinstrasser | 252/299 |
| 4,009,934 | 3/1977 | Goodwin et al. | 252/299 |
| 4,027,950 | 6/1977 | Moriyama et al. | 252/299 |
| 4,029,594 | 6/1977 | Gavrilovic et al. | 252/299 |
| 4,047,803 | 9/1977 | Yaguchi et al. | 252/299 |
| 4,058,477 | 11/1977 | Doller et al. | 252/299 |
| 4,058,478 | 11/1977 | Doller et al. | 252/299 |

FOREIGN PATENT DOCUMENTS

4962390 6/1974 Japan ...................... 252/299

OTHER PUBLICATIONS

Dave; J. S., et al., "Mesomorphic Behavior of Schiff Base Ester," Abst: I-20, 6th Int. Liq. Cryst. Conf., Kent, Ohio (Aug 23-27, 1976).
Kast, Landolt-Bornstein, vol. 2, part 2a, 6th Edition, Springer-Verlac, Berlin, pp. 266-267, 300, 300 (1960).
Castellano; J. A., et al., J. Org. Chem., vol. 33, No. 9, pp. 3501-3504 (1968).
Gray; G. W., et al., "Liquid Crystals & Plastic Crystals," John Wiley and Sons, Inc., N. Y., pp. 103-152 (1974).

*Primary Examiner*—Benjamin R. Padgett
*Assistant Examiner*—T. S. Gron
*Attorney, Agent, or Firm*—Oblon, Fisher, Spivak, McClelland & Maier

[57] ABSTRACT

Liquid crystalline compounds of the formula:

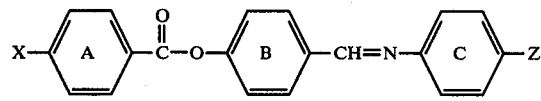

wherein X is an electron-repelling radical and Z is an electron-attracting radical, and rings A, B and C are each unsubstituted or additionally substituted with 1 to 4 identical or different monovalent organic radicals.

4 Claims, No Drawings

LIQUID CRYSTALLINE COMPOUNDS

BACKGROUND OF THE INVENTION

1. Field of the Invention

The present invention relates to novel compounds useful in liquid crystal displays, their preparation and novel intermediates.

2. Description of the Prior Art

Liquid crystal mixtures having a positive dielectric constant anisotropy find particular utility in electro-optic cells. Examples of such liquid crystal (L.C.) mixtures are described in DT-PS- No. 2,321,632. An important parameter for the operation of LC-displays is the width of the crystalline mesophase as determined by the difference between the transformation temperature crystalline/liquid crystalline (i.e., C/L temperature) or the crystalline/nematic (C/N) temperature, on one hand and the liquid crystalline/isotropic (LC/I) transformation temperature or nematic/isotropic (N/I) transformation temperature on the other hand. Also important is the threshold voltage, $V_s$, which determines the voltage necessary for the operation of the L.C. cell which is dependent on the magnitude of the positive dielectric constant anisotropy. The consistency or viscosity as well as the chemical and physical stability of liquid crystal mixture also influences the operation of L.C. displays.

These parameters may be partially influenced by the particular components and their concentration in the liquid crystal mixture. However, many of the components or additives disclosed in the prior art which may favorably affect one of the parameters, e.g., the width of the mesophase, have deleterious effect on one or more of the other parameters; e.g., the magnitude of the positive dielectric anisotropy.

The complexity of liquid crystal mixtures increases as the number of components increases. The increasing complexity can lead to irreversible changes during the use of such mixtures, for example, short-term supercooling may cause crystallization or chromatagraphic-type dissociation phenomena.

A satisfactory solution to this problem has not been found and research continues for L.C. compounds, L.C. mixtures and components which impart the desired operating characteristics with the fewest possible active compounds wherein compounds which favorably influence one parameter do not adversely effect another parameter.

As additives for raising the clearing point of LC-mixtures with overall positive DC-anistropy or compensating the clearing point depressing action of other components, i.e., for generally stabilizing the mesophase - there is known a group of aromatic compounds with three nuclei in a linear arrangement according to the formula (10)

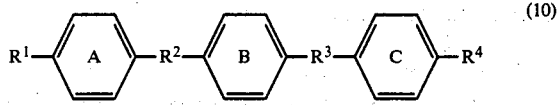

wherein $R^1$, $R^2$, $R^3$ and $R^4$ have the significance given below and the rings A, B, C carry additional substituents as necessary:

According to DT-OS No. 2,321,623 these are used as additives for LC-mixtures compounds of the formula (10) in which the $R^1$ and $R^4$ groups indicate linear-chain alkyl- or alkoxy-radicals with 1-8 C-atoms, and the groups $R^2$ and $R^3$ are carbonyloxy-groups

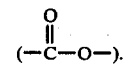

DT-OS No. 2,450,088 discloses additives for LC-mixtures compounds of the formula (10) in which $R^1$ and $R^4$ are linear-chain alkyl- or alkoxy-groups with 1-8 C-atoms, $R^2$ is a single bond and $R^3$ is the carbonyloxy-radical or the oxycarbonyl one

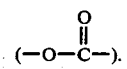

DT-OS No. 2,502,904 also discloses additives for LC-mixtures, among others, such compounds of the formula (10) in which $R^1$ is an alkyl-, alkoxy-, acyloxy- or alkoxycarbonyloxy-radical, $R^4$ is the same as $R^1$ or is the nitrile-group and $R^2$ and $R^3$ are carbonyloxy-groups or single bonds.

In DT-OS No. 2,545,121 there are disclosed as additives for LC-mixtures such compounds of the formula (10) in which a. $R^1$ is an alkyl-radical with 4–8 C-atoms, $R^2$ is a single bond, $R^3$ is the carbonyloxy-group and $R^4$ is the nitrile-group, or b. $R^1$ is an alkoxy-radical, $R^2$ is the carbonyloxy-group, $R^3$ is the oxycarbonyl-group and $R^4$ is an alkoxy-radical, or c. $R^1$ is an alkoxy-radical, $R^2$ is the methinazo-group (—CH=N—), $R^3$ is the azomethin-group (—N=HC—) and $R^4$ is an alkoxy-radical.

In connection with the compounds (b.) and (c.) it is pointed out in DT-OS No. 2,545,121 that these, in contrast to the compounds (a.), have a negative dielectric constant anisotropy and are not suited to field effect cells.

U.S. Pat. No. 3,951,846 also discloses compounds of the formula (10) described as being suited for nematic LC-displays, where $R^1$ is the hydrogen atom or an alkyl-, alkoxy-, acyloxy- or alkyloxy-carbonyloxy-radical, $R^2$ is the carbonyloxy-group, $R^3$ is a single bond and $R^4$ is the nitrile-group.

These known compounds do permit more or less stabilization or extension of the mesophase to higher temperatures, but do not possess a positive dielectric anisotropy or too small a positive dielectric constant anisotropy. For the commercially significant known LC-displays with twisted nematic phases (field-effect rotation cell), LC-mixtures with overall high positive dielectric constant anisotropy, Δ ε, in the range of 10–30 or more would be advantageous.

A need therefore continues to exist for liquid crystal compounds and mixtures having a positive dielectric constant anisotropy, high clearing points and wide mesophases.

SUMMARY OF THE INVENTION

Accordingly, it is one object of the present invention to provide liquid crystal compounds having a positive dielectric anisotropy.

Another object of the present invention is to provide liquid crystal mixtures having a magnitude Δ ε of positive dielectric anisotropy of from 10 to 30 or greater.

Still another object of the present invention is to provide liquid crystal compounds having high clearing points.

Yet another object of the present invention is to provide liquid crystal compounds having a wide mesophase.

These and other objects of the present invention which will become obvious from the disclosure have been attained by providing compounds which comprise three phenylene rings in an essentially linear arrangement joined together by a carbonyloxy group and a azomethine group respectively.

DESCRIPTION OF THE PREFERRED EMBODIMENTS

The preferred compounds of the present invention have the formula:

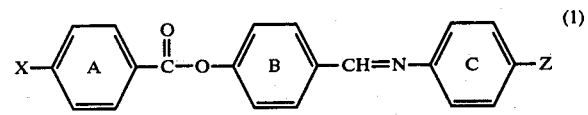
(1)

in which X is an electron-repelling radical such as a hydrogen atom, alkyl-, alkoxy-, alkylcarbonyloxy-, alkyloxycarbonyloxy-, amino-, N-monoalkylamino-, N,N-dialkylamino- or N-formyl-N-alkylamino- groups in which the alkyl-radicals have 1-8 C-atoms in predominantly practically linear chains and Z is an electron-attracting radical, such as nitrile-, nitro-, methylsulfonyl-, trifluormethyl-, sulfonyl- or N-acylamino-groups, the acyl-radical of which contains 1-9 C-atoms, and the rings A, B, C each can have, independently from one another, one or more additional substituents, such as halogen atoms, like chlorine, fluorine or bromine, the nitrile- or methyl-groups. Preferably at most one of the rings A, B, C is additionally substituted. The alkyl- or acyl-containing examples of X or Z mostly lower alkyl-groups (1-6 C-atoms) are preferred.

The LC-compounds (1) are prepared according to this invention by way of the new intermediate compounds (14) or (14') by the following synthesis scheme:

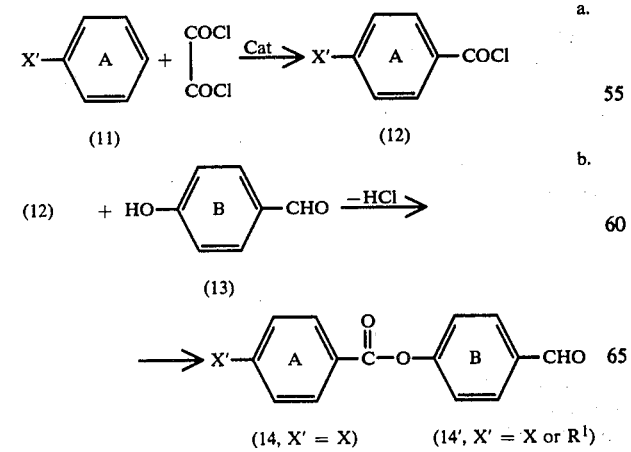

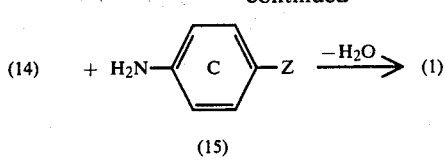

where A, B, C and Z have the significance given above and X' is the same as X when the new compounds (1) are produced, or can even be the groups given above for R¹ when the new aldehydes (14, 14') are to be used as such or as intermediate compounds for the synthesis of known compounds (10). In this scheme, the following is to be noted:

a. The reaction of compounds (11) with acid chlorides in the presence of catalysts, in particular Friedel-Crafts catalysts such as AlCl₃, to form compounds (12) is known and can advantageously be achieved by the method described by M. Neubert et al, in Liquid Crystals and Ordered Fluids, 2 (1974), 293–305 with good yield (50%) using oxalyl chloride as the acid chloride.

b. The reaction of compounds (12) with p-hydroxybenzaldehyde is an esterification known in the art, preferably carried out in the presence of an acid acceptor, like pyridine. The compounds (14') have not previously been described and are nematic liquid crystals. Examples are given in the following Table I.

TABLE I

| Compound of Formula (14') X' | C | (°C.) | N | (°C.) | I |
|---|---|---|---|---|---|
| n-C₃H₇ | . | 45 | . | (11) | . |
| n-C₄H₉ | . | 48 | . | ( 7) | . |
| n-C₅H₁₁ | . | 33.5 | . | (24) | . |

The new compounds (14') are suited not only for intermediate compounds in the production of the new compounds (1), but also for a synthesis of the known compounds (10) improved with respect to the state-of-the-art, where each of the bridge groups R² and R³ is a carbonyloxy-group. For this one can oxidize the aldehyde compounds (14') by straightforward known methods with practical quantitative yields to corresponding carboxylic acids of the formula (16)

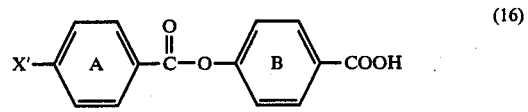
(16)

where X'=X or R¹, and then use these in a known manner to form the corresponding three-nuclei compound (10).

For the production of the compounds (16) comparatively complicated synthesis procedures have been required until now as evidenced by the literature (Mol. Cryst. Liqu. Cryst. (1974), vol. 2, pp. 7–9).

In general, according to the invention, the new compounds of the formula (14), when X'=X, or of the formula (14'), when X'=X or R¹, can be obtained by transformation of compounds of the formula (12')

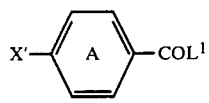

in which L¹ is a separable monovalent group, e.g., a halogen atom such as chlorine, with compounds of the formula (13')

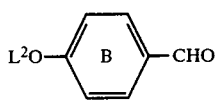

in which L² is a monovalent group which can react with the L¹ radical, e.g., the hydrogen atom, with the splitting off of L¹L².

c. The condensation of the compound (14) with the corresponding p-substituted aniline (15) can be carried out in straightforward known methods for production of Schiff bases. The compounds (15) are known as such. Isolation and purification of the new compounds (1) obtained in step (c.) can be done by straightforward methods. Examples of the new compounds (1) are given in Table II.

TABLE II

| Compound of the Formula (1) X | Z | C | (°C.) | N | (°C.) | I |
|---|---|---|---|---|---|---|
| n-C₃H₇ | CN | . | 138 | . | 285 | . |
| n-C₄H₉ | CN | . | 126.5 | . | 275 | . |
| n-C₅H₁₁ | CN | . | 107 | . | 282 | . |

The new LC-compounds (1) are easily produced and possess very high clearing points or offer mesophases which can be characterized as very wide (>100° C.) in comparison to the known compounds (10). Since the dipole moments of the substituents X, Z, —COO—, —CH=N— of the compounds (1) act in the same direction, a high positive dielectric constant anisotropy results.

The new LC-compounds of the formula (1) are used in accordance with the invention for LC-mixtures, which exhibit overall a high positive dielectric constant anisotropy and the desired mesophase width.

The new LC-compounds are suitable for the dielectric of the known field-effect cells with a twisted nematic phase and for known LC-displays which work according to the so-called guest/host effect (see e.g., B. G. Heilmeier et al, Mol. Cryst. and Liqu. Cryst. (1969), vol. 8, pp 293-304).

EXAMPLE 1

Oxalyl chloride (38 g) was added to a stirred mixture of AlCl₃ (40 g) and tetrachloroethane (450 ml). n-butylbenzene (40 g) was added to this mixture and stirred for 30 minutes at room temperature. The reaction mixture was then poured on ice, the organic phase separated, washed with water and dried over sodium sulfate. The solvent was driven off and the 4-n-butylbenzoyl chloride distilled under vacuum 155°/25 Torr.

The acid chloride (4.9 g) was added to a solution of 4-hydroxybenzaldehyde (3 g) in 40 ml pyridine and stirred for 2 hours. The reaction mixture was then poured on a solution of 65 ml conc HCl in 200 ml ice water and the product extracted with ether. The ethereal extract was washed neutral, dried and the solvent driven off to get the product which was purified by distillation 180°/0.01 Torr.

The so obtained aldehyde (6.9 g) was heated together with aminobenzonitrile (4.2 g) for 3 hours at 110° C. and 30 Torr. The unreacted material was distilled off at 170°/0.1 Torr to obtain almost pure Schiff's base in 83% yield. The Schiff's base was crystallized from CCl₄.

EXAMPLE 2

Oxalyl chloride (38 g) was added to a stirred mixture of AlCl₃ (40 g) trichloroethylene (450 ml) and n-pentylbenzene (44 g). After a reaction time of 30 minutes, the mixture was poured on ice and the organic layer separated, washed, and dried. The 4-n-pentylbenzoyl chloride was then distilled under vacuum 83°/0.1 Torr.

The esterification was carried out as described under Example 1, paragraph 2.

The aldehyde (28 g) was heated together with aminobenzonitrile (11 g) at 150° C. and 30 Torr for 2 hours. The unreacted substances were removed at 180° C./0.1 Torr and the Schiff's base was obtained in 90% yield. The product was crystallized from benzene.

Having now fully described this invention, it will be apparent to one of ordinary skill in the art that many changes and modifications can be made thereto without departing from the spirit or scope of the invention set forth herein.

What is claimed as new and intended to be covered by Letters Patent of the U.S. is:

1. Nematic liquid crystalline compounds of the formula:

wherein X is C₁–C₈ alkyl and Z is cyano.

2. The compounds of claim 1, wherein said alkyl radical contains 3-6 carbon atoms.

3. A liquid crystal mixture characterized by a high overall positive dielectric anisotropy and a stable nematic mesophase which comprises at least one compound of the formula:

wherein X is C₁–C₈ alkyl and Z is cyano; and
one or more additional compounds which will not interfere with said stable mesophase and said high overall positive dielectric anisotropy.

4. The mixture of claim 3, wherein said alkyl group contains 3-6 carbon atoms.

* * * * *